(12) United States Patent
Hunt

(10) Patent No.: US 10,578,562 B2
(45) Date of Patent: Mar. 3, 2020

(54) ACTIVE REAL-TIME CHARACTERIZATION SYSTEM USING RADIO-FREQUENCY RADIATION

(71) Applicant: The Boeing Company, Chicago, IL (US)

(72) Inventor: Jeffrey H. Hunt, Thousand Oaks, CA (US)

(73) Assignee: THE BOEING COMPANY, Chicago, IL (US)

( * ) Notice: Subject to any disclaimer, the term of this patent is extended or adjusted under 35 U.S.C. 154(b) by 191 days.

(21) Appl. No.: 15/902,225

(22) Filed: Feb. 22, 2018

(65) Prior Publication Data

US 2019/0257769 A1 Aug. 22, 2019

(51) Int. Cl.
*G01N 22/02* (2006.01)

(52) U.S. Cl.
CPC ................... *G01N 22/02* (2013.01)

(58) Field of Classification Search
CPC ...... G01N 22/00; G01N 22/02; G01F 23/284; G01R 27/04; G01R 31/11
See application file for complete search history.

(56) References Cited

U.S. PATENT DOCUMENTS

| 5,973,778 A | 10/1999 | Hunt |
| 6,781,686 B2 | 8/2004 | Hunt |
| 6,788,405 B2 | 9/2004 | Hunt |
| 6,795,175 B2 | 9/2004 | Hunt |
| 6,798,502 B2 | 9/2004 | Hunt |
| 6,819,844 B2 | 11/2004 | Hunt |
| 7,289,656 B2 | 10/2007 | Hunt |
| 7,304,305 B2 | 12/2007 | Hunt |
| 7,757,558 B2 | 7/2010 | Bossi et al. |
| 7,983,469 B2 | 7/2011 | Engelbart et al. |
| 8,664,583 B2 | 3/2014 | Hunt et al. |
| 8,789,837 B2 | 7/2014 | Chang et al. |
| 2013/0048841 A1 | 2/2013 | Hunt et al. |
| 2013/0050685 A1 | 2/2013 | Hunt et al. |
| 2016/0119557 A1* | 4/2016 | Hunt .................... H04N 5/2256 348/131 |

* cited by examiner

*Primary Examiner* — Jermele M Hollington
*Assistant Examiner* — Suresh K Rajaputra
(74) *Attorney, Agent, or Firm* — Moore Intellectual Property Law, PLLC

(57) ABSTRACT

A system for providing active real-time characterization of an article under test is disclosed. First, second and third RF radiation sources each outputs and directs a beam of RF radiation at a particular area on the article under test. An RF receiver and a second harmonic generation RF receiver, a sum frequency receiver, and a third order receiver are each configured to receive a respective predetermined return beam of RF radiation from the particular area on the article under test. A processor receives signals from the receivers and calculates in real time respective spectroscopic signals and compares each calculated signal with each other calculated signal and with a predetermined baseline signal to ensure that the article under test conforms to an expected value.

20 Claims, 2 Drawing Sheets

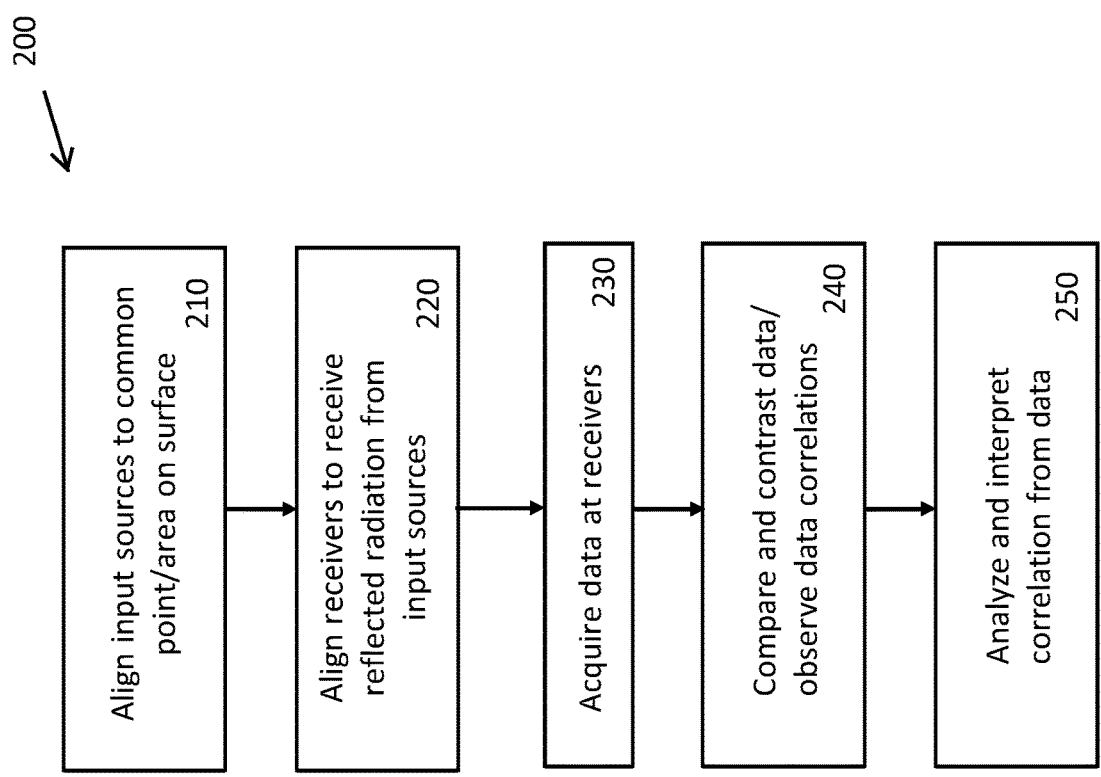

ACTIVE REAL-TIME CHARACTERIZATION SYSTEM USING RADIO-FREQUENCY RADIATION

FIELD

This disclosure relates generally to an active real-time characterization system based on radio-frequency radiation for use during composite overlay manufacturing.

BACKGROUND

In recent years, aircraft manufacturers have developed aircraft designs and aircraft fabrication methods that make greater use of carbon fiber composite materials and the like ("composite materials" or "CFCM"), such as graphite/epoxy, carbon fiber reinforced plastic ("CFRP") and graphite reinforced polymer ("GRP"). Composite materials are significantly lighter than traditional aircraft materials (e.g. aluminum, titanium, steel and alloys thereof), and can provide high strength with low weight, allowing lighter, more fuel efficient aircraft. In some newer aircraft, for example, the majority of the primary structure, including the fuselage and wing, is made of composite materials. One drawback in the growing use of carbon fiber composite materials is the lack of effective non-destructive evaluation type testing methodologies available for testing such materials during and after manufacture. In particular, there is a lack non-destructive evaluation type testing systems for providing real time characterization of composites during overlay manufacturing.

Accordingly, there is a need for a testing system which addresses the drawbacks identified above.

SUMMARY

In a first aspect, a system provides active real-time characterization of an article under test. A first RF source outputs a first beam of RF radiation at a first pre-determined frequency. The first RF source is configured to direct the first beam of RF radiation at a particular area on the article under test. An RF receiver is configured to receive a first predetermined return beam of RF radiation from the particular area on the article under test. Finally, a processor is coupled to receive and process signals from the RF receiver to ensure that the article under test conforms to an expected value.

In a further embodiment, the processor may be configured to calculate in real time a linear spectroscopic signal and to compare the calculated linear spectroscopic signal with a predetermined baseline signal to ensure that the article under test conforms to the expected value.

In another further embodiment, a second RF source may output a second beam of RF radiation at a second pre-determined frequency. The second RF source may be configured to direct the second beam of RF radiation at the same particular area on the article under test. A second harmonic generation RF receiver may be configured to receive a second predetermined return beam of RF radiation from the particular area on the article under test. The processor may be coupled to receive and process signals from the second harmonic generation RF receiver and may be configured to calculate in real time a second harmonic generation spectroscopic signal and to compare the calculated linear spectroscopic signal with each other calculated signal and with a predetermined baseline signal to ensure that the article under test conforms to the expected value.

In yet another further embodiment, a sum frequency RF receiver may be configured to receive a third return beam of RF radiation from the particular area on the article under test. The processor may be coupled to receive and process signals from the sum frequency RF receiver and may be configured to calculate in real time a sum-frequency spectroscopic signal and to compare the calculated sum-frequency spectroscopic signal with each other calculated signal and with a predetermined baseline signal to ensure that the article under test conforms to the expected value.

In a still further embodiment, a third RF source may output a third beam of RF radiation at a third pre-determined frequency. The third RF source may be configured to direct the third beam of RF radiation at the same particular area on the article under test. A third order RF receiver may be configured to receive a fourth return beam of RF radiation from the particular area on the article under test. The processor may be coupled to receive signals from the third order RF receiver and may be configured to calculate in real time a third order spectroscopic signal and to compare the third order spectroscopic signal with each other calculated signal and with a predetermined baseline signal to ensure that the article under test conforms to the expected value.

In a second aspect, a method for active real-time characterization of an article under test. A first RF radiation source is directed at an area on a surface of the article under test. An RF receiver is aligned to receive RF radiation reflected from the surface of the article under test. Signals are acquired from the RF receiver based on the received RF radiation. Finally, the signals from the RF receiver are processed to ensure that the article under test conforms to an expected value.

In a further embodiment, a linear spectroscopic signal may be calculated in real time and the calculated linear spectroscopic signal may be compared with a predetermined baseline signal to ensure that the article under test conforms to the expected value.

In another further embodiment, a second RF radiation source may be directed at the same area on the surface of the article under test. A second harmonic generation RF receiver may be aligned to receive RF radiation reflected from the surface of the article under test. A second harmonic generation spectroscopic signal may be calculated in real time and the calculated linear spectroscopic signal may be compared with each other calculated signal and with a predetermined baseline signal to ensure that the article under test conforms to the expected value.

In yet another further embodiment, a sum frequency RF receiver may be aligned to receive RF radiation reflected from the surface of the article under test. A sum-frequency spectroscopic signal may be calculated in real time and the calculated sum-frequency spectroscopic signal may be compared with each other calculated signal and with a predetermined baseline signal to ensure that the article under test conforms to the expected value.

In a still further embodiment, a third RF radiation source may be directed at the same area on the surface of the article under test. A third order RF receiver may be aligned to receive RF radiation reflected from the surface of the article under test. A third order spectroscopic signal may be calculated in real time and the third order spectroscopic signal may be compared with each other calculated signal and with a predetermined baseline signal to ensure that the article under test conforms to the expected value.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which:

FIG. 2 is a flow chart of a method for operating the active real-time characterization system of the present disclosure.

DETAILED DESCRIPTION

Figure 1:
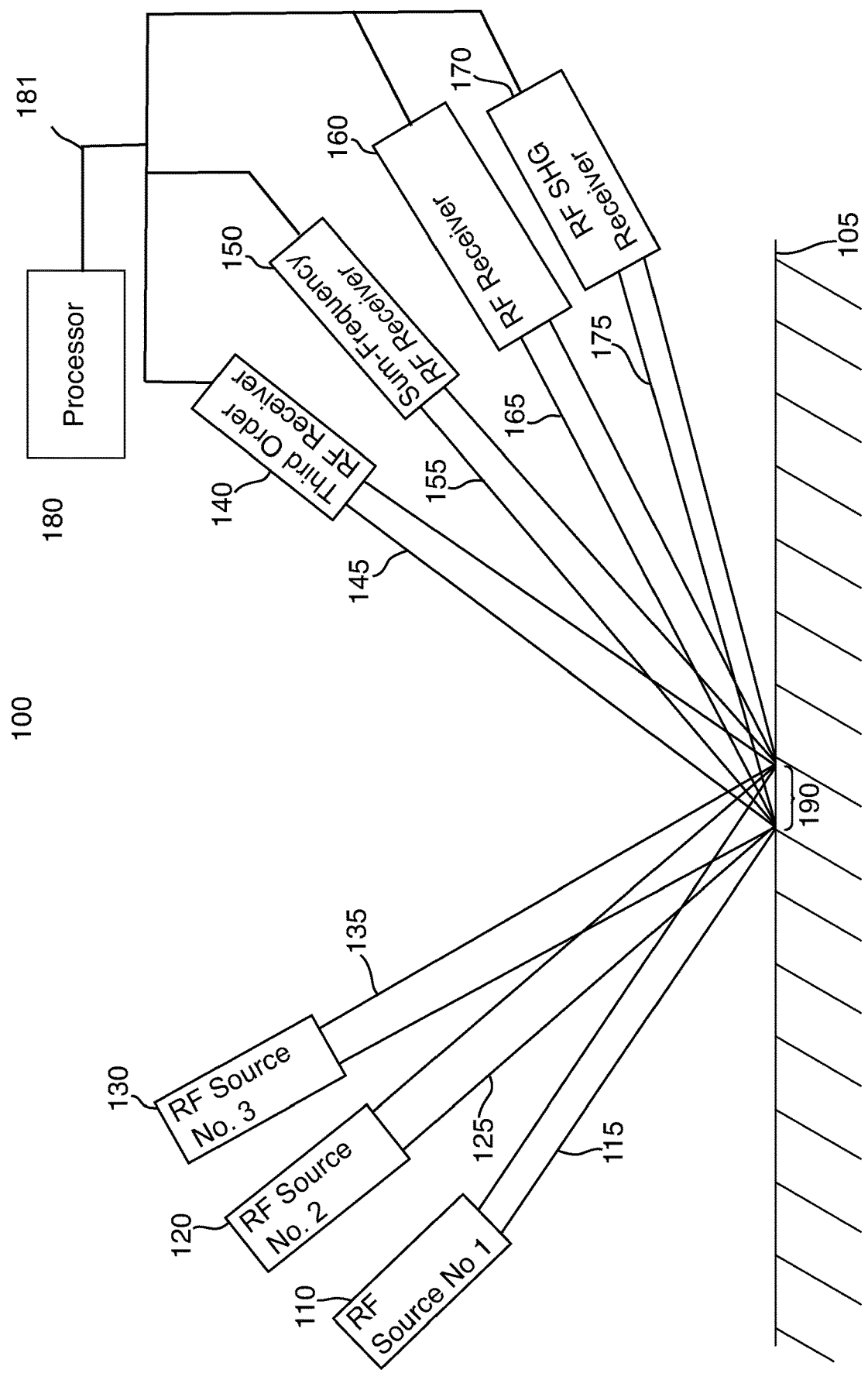
FIG. 1 is a block diagram of an active real-time characterization system for use during composite overlay manufacturing according to an aspect of the present disclosure.

In the present disclosure, like reference numbers refer to like elements throughout the drawings, which illustrate various exemplary embodiments of the present disclosure.

Referring now to FIG. 1, the active real-time characterization system 100 of the present disclosure includes a first radio-frequency (RF) radiation source 110, a second RF radiation source 120, and a third RF radiation source 130. Each of the radiation sources 110, 120, 130 is positioned to transmit a beam (i.e., rays) of RF radiation at an area 190 on a surface of an article under test 105, e.g., a part constructed from carbon-fiber composites. In particular, first RF source 110 is positioned to direct a beam of RF radiation 115 at area 190, second RF source 120 is positioned to direct a beam of RF radiation 125 at area 190, and third RF source 130 is positioned to direct a beam of RF radiation 135 at area 190. First RF source 110 is configured to output radiation at a first fixed, predetermined frequency, while second RF source 120 is configured to output radiation at a second fixed, predetermined frequency, and third RF source 130 is configured to output radiation at a third fixed, predetermined frequency. Each of the fixed, predetermined frequencies are different from each other of the fixed, predetermined frequencies. The RF frequencies output by the RF radiation sources 110, 120, 130 may range through the entire RF range (including microwave frequencies) of 3 kHz to 300 GHz.

System 100 in FIG. 1 also includes a number of receivers for receiving radiation reflected from the surface of article under test 105, including a Raman (third order) receiver 140 which receives a radiation beam 145 and a sum-frequency receiver 150 which receives a radiation beam 155. System 100 also includes an RF receiver 160 which receives a radiation beam 165 and a second harmonic generation (SHG) RF receiver 170 which receives a radiation beam 175. Although four separate receivers 140, 150, 160, 170 are shown in FIG. 1, in an alternative embodiment a single receiver may be used and the received signals may be processed to extract the separate signals that would be provided by the four separate receivers 140, 150, 160, 170 (e.g., by bandpass filtering). Each of the receivers 140, 150, 160, 170 produces an output signal that is communicated in a conventional manner to a processor 180 in FIG. 1 via a link 181 for processing as discussed below. As also discussed below, the reflected radiation beams 145, 155, 165 and 175 are at a particular angle with respect to the surface of device under test 105 based on the fixed angles that radiation beams 115, 125 and 135 are directed at the surface of device under test 105. The receivers 140, 150, 160, 170 are thus positioned to receive such radiation beams. Each receivers 140, 150, 160, 170 is a conventional RF receiver for receiving RF beams at particular expected frequencies.

As one of ordinary skill in the art will readily recognize, RF sources 110, 120, 130 and receivers 140, 150, 160, 170 may be fixed in place and article under test 105 may be moved so that the area 190 of the radiation beams 115, 125, 135 moves over the entire surface of article under test 105. In another embodiment, RF sources 110, 120, 130 and receivers 140, 150, 160, 170 may be mounted on a fixture that moves along the surface of article under test 105. In yet another embodiment, RF sources 110, 120, 130 may be arranged to raster the respective output radiation beams 115, 125, 135 across the surface of the article under test 105, and the receivers 140, 150, 160, 170 arranged to move proportionally to receive the respective associated return radiation beams 145, 155, 165, 175.

In operation, the system 100 shown in FIG. 1 provides a combination of linear spectroscopy, second order surface frequency mixing spectroscopy, and third order nonlinear (e.g., Raman spectroscopy) spectroscopy. System 100 provides a number of ways of performing species identification and allows the cross correlation between the three types of spectroscopies in order to avoid false negative spectral features.

In particular, first RF source 110 and second RF source 120 are configured and positioned to provide RF beams which allow the processor 180 to generate simultaneous linear (same frequency) and non-linear (second harmonic generation) real time spectroscopic signals, in conjunction with RF receiver 160 and SHG RF receiver 170. As one of ordinary skill in the art will readily recognize, RF receiver 160 and SHG RF receiver 170 are positioned at a particular predetermined angle to receive the appropriate respective return RF beams 165, 175 from surface of the article under test 105.

Further, first RF source 110 and second RF source 120 are also configured and positioned to provide RF beams which allow the processor 180 to generate a sum-frequency ($\omega_{IR}+\omega_{VISIBLE}$) real-time spectroscopic signal, in conjunction with sum-frequency receiver 150. As one of ordinary skill in the art will readily recognize, sum-frequency receiver 140 is positioned at a particular predetermined angle to receive the appropriate return RF beams 155 from surface of the article under test 105.

Finally, second RF source 120 and third RF source 130 are configured and positioned to provide RF signals which allow the processor 180 to generate a third-order ($2\omega_{VIS1}-\omega_{VIS2}$) (e.g., Raman) real-time spectroscopic signal, in conjunction with Raman (third order) receiver 140. As one of ordinary skill in the art will readily recognize, Raman (third order) receiver 140 is positioned at a particular predetermined angle to receive the appropriate return RF beams 145 from surface of the article under test 105.

The processor 180 is coupled to receive signals from each of receivers 140, 150, 160, 170 and is configured to calculate in real time a linear spectroscopic signal, a second harmonic generation spectroscopic signal, a sum-frequency spectroscopic signal and a third order spectroscopic signal. The processor 180 is also configured to compare each calculated signal with each other calculated signal and with a predetermined baseline signal to ensure that the article under test conforms to an expected value. When the processor 180 determines that the calculated signals indicate that the article under test does not conform to the expected value, processor 180 provides a fault signal which may be used to halt formation of the part of the article under test 105 for either repair thereof or so that part of the article under test 105 may be immediately discarded.

Referring now to FIG. 2, a flow chart 200 of a method for operating the active real-time characterization system of the present disclosure is shown. In step 210, the RF sources are aligned to a common point or area on the surface of the article under test. Next, at step 520, the receivers are aligned to receive radiation reflected from the RF sources. As evident from the discussion above, the third order receiver 140, the sum-frequency receiver 150, the RF receiver 160, and the SHG RF receiver are aligned separately. Further, at step 530, data is acquired at each of the receivers. After this, at step 540, the acquired data is compared and contrasted, and correlations among the data are observed. Finally, at step 550, the correlations among the data are analyzed and interpreted to determine whether or not the composition of the article under test falls within expected ranges.

As one of ordinary skill in the art will readily recognize, the active-real time characterization system 100 of the present disclosure may be applied to testing for composition of the article under test, for identifying contamination on the surface of the article under test or for a combination of both material composition and contamination identification. In addition, the active real-time characterization system 100 of the present disclosure may be used to test graphite fiber-based materials, polymer/plastic materials, glass fiber reinforcement-based materials such as fiberglass and glass laminate aluminum reinforced epoxy ("GLARE"), resins, plastics or polymers without reinforcement fibers, metals, and ceramics including glass materials.

By providing a combination of linear, non-linear, sum-frequency and third order real time spectroscopic signals, the present system provides the ability to more accurately monitor the chemistry of composite parts during formation by avoiding false negative spectral features. This system can allow, in some cases, defects to be repaired and thus prevent the loss of the composite part. In other cases, this system can ensure that production is halted as soon as a defect is identified, and thus preventing further costly work from being performed on a composite part destined to be discarded.

In further embodiments, the data generated by the active-real time characterization system 100 of the present disclosure may be combined for analysis with data separately generated by way of RF spectroscopy, microwave spectroscopy, THz spectroscopy, ultrasonic NDE/NDI, Third order RF mixing spectroscopy, and/or ellipsometry.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A system for providing active real-time characterization of an article under test, comprising:
   a first RF source for outputting a first beam of RF radiation at a first pre-determined frequency, the first RF source configured to direct the first beam of RF radiation at a particular area on the article under test;
   an RF receiver configured to receive a first predetermined return beam of RF radiation from the particular area on the article under test; and
   a processor coupled to receive and process signals from the RF receiver to ensure that the article under test conforms to an expected value.

2. The system of claim 1, wherein the processor is configured to calculate in real time a linear spectroscopic signal and to compare the calculated linear spectroscopic signal with a predetermined baseline signal to ensure that the article under test conforms to the expected value.

3. The system of claim 2, further comprising:
   a second RF source for outputting a second beam of RF radiation at a second pre-determined frequency, the second RF source configured to direct the second beam of RF radiation at the same particular area on the article under test.

4. The system of claim 3, further comprising:
   a second harmonic generation RF receiver configured to receive a second predetermined return beam of RF radiation from the particular area on the article under test.

5. The system of claim 4, wherein the processor is coupled to receive and process signals from the second harmonic generation RF receiver and is configured to calculate in real time a second harmonic generation spectroscopic signal and to compare the calculated linear spectroscopic signal with each other calculated signal and with a predetermined baseline signal to ensure that the article under test conforms to the expected value.

6. The system of claim 5, further comprising:
   a sum frequency RF receiver configured to receive a third return beam of RF radiation from the particular area on the article under test.

7. The system of claim 6, wherein the processor is coupled to receive and process signals from the sum frequency RF receiver and is configured to calculate in real time a sum-frequency spectroscopic signal and to compare the calculated sum-frequency spectroscopic signal with each other calculated signal and with a predetermined baseline signal to ensure that the article under test conforms to the expected value.

8. The system of claim 7, further comprising:
   a third RF source for outputting a third beam of RF radiation at a third pre-determined frequency, the third RF source configured to direct the third beam of RF radiation at the same particular area on the article under test.

9. The system of claim 8, further comprising:
   a third order RF receiver configured to receive a fourth return beam of RF radiation from the particular area on the article under test.

10. The system of claim 9, wherein the processor is coupled to receive signals from the third order RF receiver and is configured to calculate in real time a third order spectroscopic signal and to compare the third order spectroscopic signal with each other calculated signal and with a predetermined baseline signal to ensure that the article under test conforms to the expected value.

11. A method for active real-time characterization of an article under test, comprising the steps of:
   directing a first RF radiation source at an area on a surface of the article under test;
   aligning an RF receiver to receive RF radiation reflected from the surface of the article under test;
   acquiring signals from the RF receiver based on the received RF radiation; and
   processing the signals from the RF receiver to ensure that the article under test conforms to an expected value.

12. The method of claim 11, wherein the processing step comprises calculating in real time a linear spectroscopic signal and comparing the calculated linear spectroscopic signal with a predetermined baseline signal to ensure that the article under test conforms to the expected value.

13. The method of claim 12, further comprising the step of:

directing a second RF radiation source at the same area on the surface of the article under test.

14. The method of claim 13, further comprising the step of:

aligning a second harmonic generation RF receiver to receive RF radiation reflected from the surface of the article under test.

15. The method of claim 14, wherein the processing step comprises calculating in real time a second harmonic generation spectroscopic signal and comparing the calculated linear spectroscopic signal with each other calculated signal and with a predetermined baseline signal to ensure that the article under test conforms to the expected value.

16. The method of claim 15, further comprising the step of:

aligning a sum frequency RF receiver to receive RF radiation reflected from the surface of the article under test.

17. The method of claim 16, wherein the processing step comprises calculating in real time a sum-frequency spectroscopic signal and comparing the calculated sum-frequency spectroscopic signal with each other calculated signal and with a predetermined baseline signal to ensure that the article under test conforms to the expected value.

18. The method of claim 17, further comprising the step of:

directing a third RF radiation source at the same area on the surface of the article under test.

19. The method of claim 18, further comprising the step of aligning a third order RF receiver to receive RF radiation reflected from the surface of the article under test.

20. The method of claim 19, wherein the processing step comprises calculating in real time a third order spectroscopic signal and comparing the third order spectroscopic signal with each other calculated signal and with a predetermined baseline signal to ensure that the article under test conforms to the expected value.

* * * * *